(12) United States Patent
Swain

(10) Patent No.: US 8,157,562 B2
(45) Date of Patent: Apr. 17, 2012

(54) ORTHODONTIC BRACKET SYSTEM AND METHOD

(75) Inventor: Ryan B. Swain, North Chili, NY (US)

(73) Assignee: Six Month Smiles Inc., Scottsville, NY (US)

( * ) Notice: Subject to any disclaimer, the term of this patent is extended or adjusted under 35 U.S.C. 154(b) by 308 days.

(21) Appl. No.: 12/536,009

(22) Filed: Aug. 5, 2009

(65) Prior Publication Data

US 2011/0033811 A1 Feb. 10, 2011

(51) Int. Cl.
*A61C 3/00* (2006.01)
(52) U.S. Cl. ............................................................. 433/9
(58) Field of Classification Search ................ 433/8–11, 433/12–15, 16–18, 22, 24, 20
See application file for complete search history.

(56) References Cited

U.S. PATENT DOCUMENTS

| | | | |
|---|---|---|---|
| 2,971,258 A | | 2/1961 | Bien |
| 3,496,637 A | * | 2/1970 | Milton ............................ 433/15 |
| 3,765,091 A | * | 10/1973 | Northcutt ......................... 433/9 |
| 3,775,850 A | * | 12/1973 | Northcutt ........................ 433/16 |
| 3,964,165 A | * | 6/1976 | Stahl ................................ 433/8 |
| 4,192,070 A | | 3/1980 | Lemchen et al. |
| 4,470,809 A | * | 9/1984 | Klepacki ......................... 433/15 |
| 4,877,398 A | | 10/1989 | Kesling |
| 4,927,362 A | | 5/1990 | Snead |
| 5,032,080 A | | 7/1991 | Hakansson et al. |
| 5,125,832 A | | 6/1992 | Kesling |
| 5,151,028 A | * | 9/1992 | Snead ............................. 433/17 |
| 5,263,859 A | | 11/1993 | Kesling |
| 5,288,229 A | * | 2/1994 | Huff et al. ....................... 433/17 |
| 5,474,444 A | * | 12/1995 | Wildman ........................... 433/8 |
| 5,516,284 A | | 5/1996 | Wildman |
| 5,556,277 A | | 9/1996 | Yawata et al. |
| 5,927,971 A | | 7/1999 | De Baets |
| 6,039,564 A | * | 3/2000 | Hendrick ......................... 433/17 |
| 6,126,441 A | | 10/2000 | Tenti |
| 6,241,516 B1 | | 6/2001 | Orikasa et al. |
| 6,428,314 B1 | | 8/2002 | Jones, Jr. et al. |
| 6,682,345 B2 | | 1/2004 | Kesling et al. |
| 6,685,468 B1 | | 2/2004 | Kesling |
| 6,705,862 B2 | * | 3/2004 | Schultz ............................ 433/17 |
| 6,786,720 B1 | | 9/2004 | Kesling et al. |
| 7,077,646 B2 | | 7/2006 | Hilliard |
| 7,104,791 B2 | | 9/2006 | Hanson |
| 2005/0069833 A1 | | 3/2005 | Chikami |
| 2005/0130094 A1 | | 6/2005 | Graham |

(Continued)

OTHER PUBLICATIONS

International Search Report and Written Opinion of the the International Search Authority dated Sep. 22, 2010, which issued in related PCT Application No. PCT/US2010/044318.

(Continued)

*Primary Examiner* — Cris L Rodriguez
*Assistant Examiner* — Hao D Mai
(74) *Attorney, Agent, or Firm* — Jeffer Mangels Butler & Mitchell LLP

(57) ABSTRACT

Disclosed herein is an orthodontic bracket system for correcting the teeth in an arch that includes molars, premolars, canines, lateral incisors and central incisors. The system includes a plurality of brackets that each include a main body portion having first and second tunnels extending transversely therethrough. Each bracket is bonded to the facial surface of a tooth in the arch. The first and second tunnels of each bracket extend approximately parallel to the facial surface of the tooth to which the bracket is bonded. The system further includes a first archwire extending through the first tunnels in each of the brackets.

22 Claims, 6 Drawing Sheets

U.S. PATENT DOCUMENTS

2006/0257810 A1 11/2006 Maijer
2008/0081310 A1 4/2008 Smith et al.

OTHER PUBLICATIONS

Printout of TP Orthodontics, Inc. "Tip-Edge Plus" Bracket Identification Charts. This document is believed to have been publicly available more than one year before the filing date of U.S. Appl. No. 12/536,009.

Image of dental bracket eyelet. This non-patent literature is believed to have been publicly available more than one year before the filing date of U.S. Appl. No. 12/536,009.

* cited by examiner

ORTHODONTIC BRACKET SYSTEM AND METHOD

FIELD OF THE INVENTION

The present invention relates generally to orthodontic bracket systems, more particularly, to orthodontic bracket systems for limited orthodontic treatment where all brackets include archwire tunnels.

BACKGROUND OF THE INVENTION

Existing bracket systems involve an open faced bracket slot as the primary slot that receives an orthodontic archwire. The archwire is placed into the open faced bracket slots and some sort of tie, door or clip is used to close the slot and hold the archwire in the slot. Existing orthodontic bracket systems that include an open faced archwire slot for archwires demand that time be taken by the operator to fasten/ligate/secure the archwire into each open slot using the ligature tie or self-ligating clip. Existing orthodontic bracket systems contain open faced bracket slots because most traditional orthodontic treatment involves the use of stainless steel wires that must be engaged in the open slot and then secured with a ligature tie, clip or door. Also, archwires associated with traditional comprehensive orthodontic treatment are typically rectangular or square and, therefore, the bracket slots are typically square or rectangular in shape. Time must also be taken at all adjustment visits to remove or disengage the ligature ties or self-ligating apparatuses on each bracket in the system. Time spent ligating and un-ligating the orthodontic archwires is the most time consuming part of orthodontic adjustment visits. Furthermore, because instruments (often sharp instruments) must be used to fasten/unfasten ligature ties or self-ligating clips, these procedures often involve some risk of injury to the patient or operator. Another disadvantage of traditional open faced orthodontic brackets is the discomfort associated with the pressure that is needed to fasten a ligature tie or open/close a self-ligating clip/door.

Accordingly, a need exists for orthodontic brackets and systems that address the problems discussed above.

SUMMARY OF THE INVENTION

The invention relates generally to an orthodontic bracket system for molars, premolars, canines, lateral incisors and central incisors. The bracket system involves the use of brackets that are essentially the same for use on all of the teeth (slight size differences may exist depending on the type of tooth on which each bracket is placed), including the anterior teeth (generally considered the front six teeth). Orthodontic treatment typically involves the use of stainless steel archwires that are not super-elastic. The present invention involves the use of closed tubular brackets on all of the teeth. The brackets are preferably used with super-elastic archwires. The inventive bracket system is specifically designed to be used for limited and/or short term orthodontic treatment that does not require stainless steel or rectangular archwires. Super-elastic wires (e.g., nickel titanium, NiTi) are preferably used for the duration of treatment in conjunction with the tubular brackets on all of the teeth (both anterior and posterior teeth). In an embodiment of the invention, the dentist has the ability to use closed faced brackets during most of the treatment where no clip, tie or the like is used, but, if desired, later in the treatment, the dentist can open up the bracket slots and put either a round wire into a converted round open slot or a rectangular wire into a rectangular open slot.

In accordance with one preferred embodiment of the present invention, there is provided a method that includes providing a plurality of orthodontic brackets that each include a main body portion having at least a first tunnel extending transversely therethrough. The main body portion is adapted to be bonded to the facial surface of a tooth such that the first tunnel extends approximately parallel to the facial surface. None of the brackets include an open faced slot. The method further includes bonding each of the plurality of brackets to separate teeth in an arch, and threading a first archwire through the first tunnel in each of the plurality of brackets.

In accordance with another preferred embodiment of the present invention, there is provided an orthodontic bracket that includes a main body portion having at least a first tunnel extending transversely therethrough, and a pair of opposing retention members extending from the main body portion. The first tunnel has a circular cross-section and the main body portion is adapted to be bonded to the facial surface of a tooth such that the first tunnel extends approximately parallel to the facial surface. In a preferred embodiment, the bracket does not include an open faced slot.

In accordance with another preferred embodiment of the present invention, there is provided an orthodontic bracket system for correcting the teeth in an arch that includes molars, premolars, canines, lateral incisors and central incisors. The system includes a plurality of brackets that each include a main body portion having at least a first tunnel extending transversely therethrough. The first tunnel has a circular cross-section and each bracket is bonded to the facial surface of a tooth in the arch. The first tunnel of each bracket extends approximately parallel to the facial surface of the tooth to which the bracket is bonded. The system also includes a first archwire extending through the first tunnels in each of the brackets. The archwire has a circular cross-section. In a preferred embodiment, none of the brackets through which the first archwire extends include an open faced slot. In another preferred embodiment, each of the brackets include a second tunnel extending transversely therethrough that extends approximately parallel to the first tunnel.

In accordance with yet another preferred embodiment of the present invention, there is provided an orthodontic bracket that includes a main body portion having first and second tunnels extending transversely therethrough. The main body portion is adapted to be bonded to the facial surface of an anterior tooth such that the first and second tunnels extend approximately parallel to the facial surface.

In accordance with yet another preferred embodiment of the present invention, there is provided an orthodontic bracket system for correcting the teeth in an arch that includes molars, premolars, canines, lateral incisors and central incisors. The system includes a plurality of brackets that each include a main body portion having first and second tunnels extending transversely therethrough. Each bracket is bonded to the facial surface of a tooth in the arch. The first and second tunnels of each bracket extend approximately parallel to the facial surface of the tooth to which the bracket is bonded. The system further includes a first archwire extending through the first tunnels in each of the brackets.

In accordance with one preferred embodiment of the present invention, there is provided a method that includes providing a plurality of orthodontic brackets that each comprise a main body portion having at least a first tunnel extending transversely therethrough and that is adapted to be bonded to the facial surface of a tooth such that the first tunnel extends approximately parallel to the facial surface, bonding each of the plurality of brackets to separate teeth in an arch, converting the first tunnel on at least one of the brackets to an open faced slot to create a slotted bracket, providing an archwire, and inserting the archwire into the slot on the slotted bracket and then threading the archwire through the first tunnel on others of the plurality of brackets.

The invention, together with additional features and advantages thereof, may be best understood by reference to the following description taken in conjunction with the accompanying illustrative drawings. In these accompanying drawings, like reference numerals designate like parts throughout the figures.

DETAILED DESCRIPTION OF THE INVENTION

Figure 1:
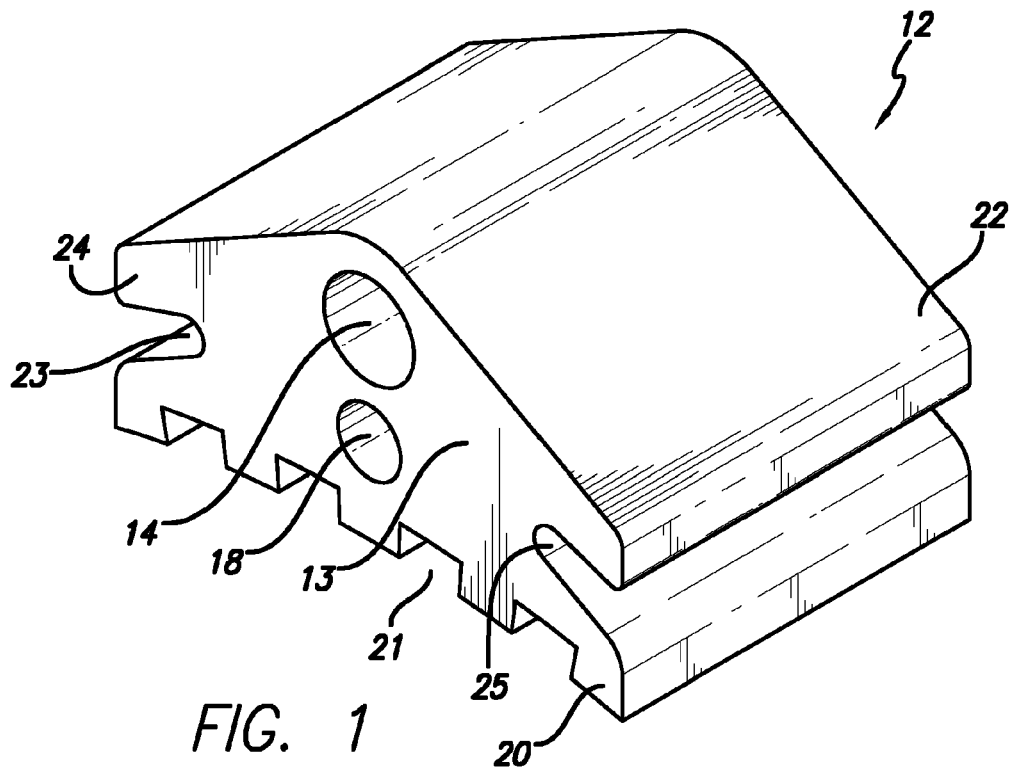
FIG. 1 is a perspective view of an orthodontic bracket having two circular archwire tunnels, in accordance with a preferred embodiment of the present invention.

As shown in the drawings, for purposes of illustration, a preferred embodiment of an orthodontic bracket system 10 is shown and described. It will be appreciated that terms such as "front," "back," "top," "bottom," "side," "up," "down," and "below" used herein are merely for ease of description and refer to the orientation of the components as shown in the figures. It should be understood that any orientation of the system 10, and the components thereof described herein is within the scope of the present invention.

Figure 2:
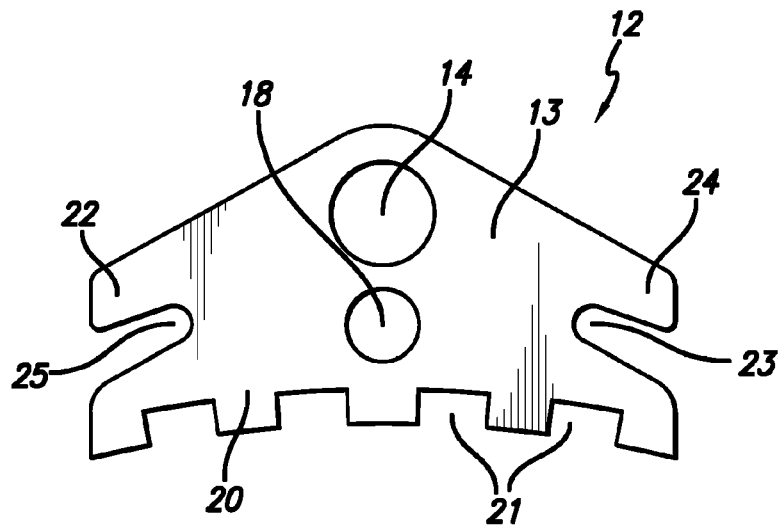
FIG. 2 is a side elevational view of the bracket of FIG. 1.
Figure 3:
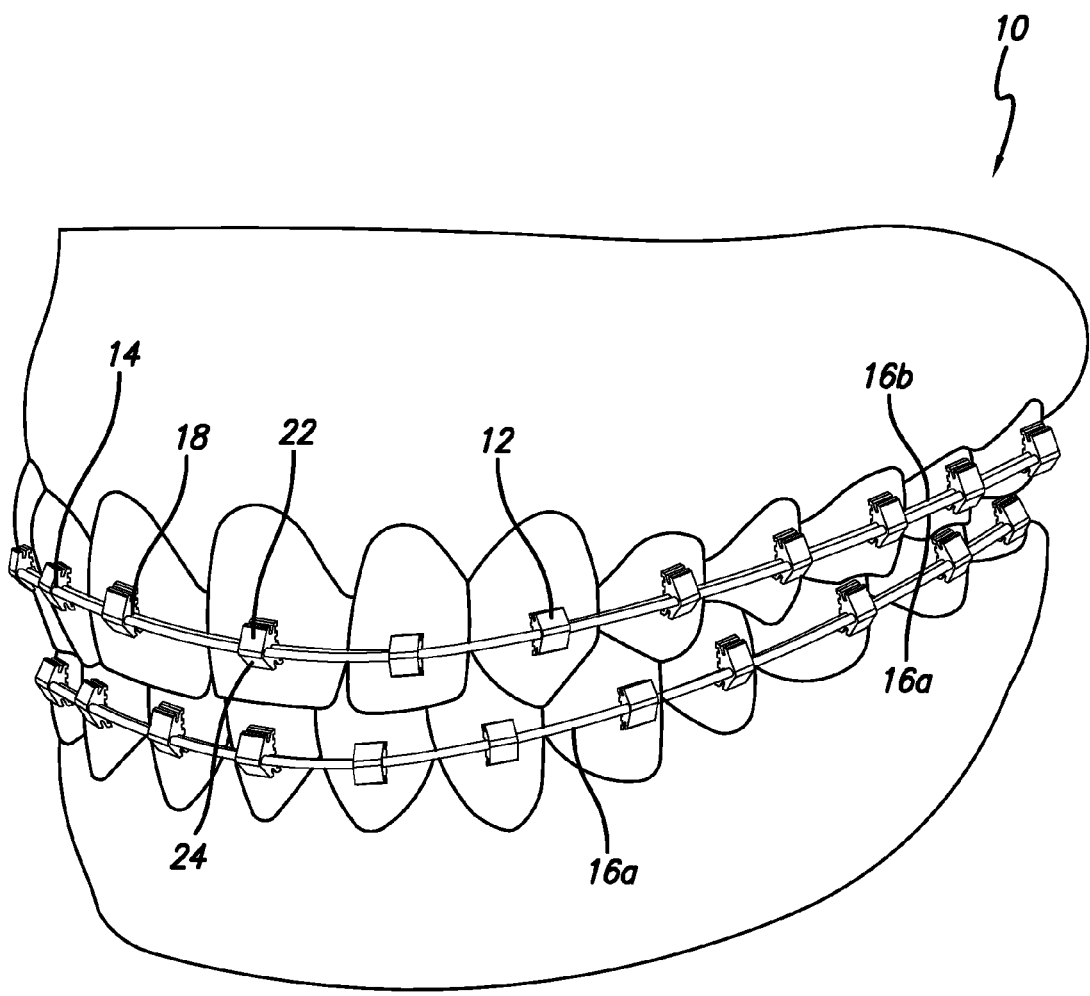
FIG. 3 is a perspective view of a plurality of the brackets shown in FIG. 1 on a set of teeth with two archwires.

Referring now to the drawings, wherein the illustrations are for purposes of illustrating the present invention and not for purposes of limiting the same, FIGS. 1-3 show a bracket 12 for use in an orthodontic bracket system 10. As shown in FIG. 1, the bracket 12 includes a main body portion 13 that has a main tunnel, tube or lumen 14 extending horizontally or transversely therethrough and is generally parallel to the occlusal surfaces of the teeth when secured to a tooth. In a preferred embodiment, the main tunnel 14 has a round cross-section rather than rectangular. As discussed above, most existing orthodontic bracket systems utilize a generally rectangular open faced slot that allows for the rectangular archwire to provide torque to the roots of the teeth as they work in conjunction with the angulations (prescriptions) that are built into the open faced archwire slot. In a preferred embodiment, the archwire or archwires 16a and 16b are round superelastic wires. This is because in a preferred embodiment, providing torque to the roots of teeth is not a component of the limited/ short term treatment goals that the system 10 is designed for.

However, in another embodiment of the invention, the tunnels 10 and 18 (discussed below) can be square, rectangular or other shape, and have corresponding archwires with a similar shape. The tunnel 14 also provides a rigid and smooth surface for the archwire 16a to slide against as it moves the teeth. Since there is no need for ligature ties (metal or elastomeric), the archwire 16a always has a smooth and hard surface to glide against. This should provide for more efficient tooth movement and less friction within the bracket system.

In a preferred embodiment of the present invention, the bracket 12 includes a secondary tunnel, lumen or archwire slot 18 that runs generally parallel to the main tunnel 14. The secondary tunnel 18 is used in the same fashion as the main tunnel 14 and is approximately the same size in diameter. However, as shown in FIG. 1, the tunnels 14 and 18 can have different diameters. As shown in FIG. 1, in a preferred embodiment, tunnel 18 is position between tunnel 10 and the base 20 or the tooth. However, this is not a limitation on the present invention. For example, in another embodiment, the tunnels 10 and 18 can be positioned in a manner such that they are both approximately the same distance from the tooth to which the bracket is bonded (i.e., side by side). In another embodiment, the bracket may include more than two tunnels.

Figure 10:
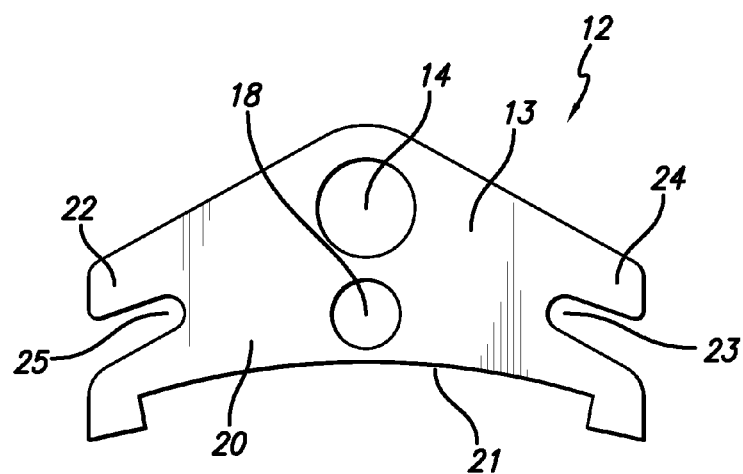
FIG. 10 is a side elevational view of the bracket of FIG. 1 with only a single undercut.

The bracket 12 includes a base 20 that includes a plurality of mesh undercuts or dovetails 21 for retentive purposes. The number of undercuts 21 is not a limitation on the present invention. As is shown in FIG. 10 in an embodiment of the invention, the base 20 can include a single undercut 21 defined therein. This can provide a stronger bond with the facial surface of the tooth because the adhesive is not broken up by the use of multiple undercuts. It will be appreciated that the base 20 is arcuately formed to generally conform to the facial surface of a tooth when the bracket 12 is bonded to a tooth in the typical manner. In a preferred embodiment, the bracket 12 also includes upper and lower wings or retention members 22 and 24. However, it should be appreciated that in another embodiment, the wings 22 and 24 may be omitted. In this embodiment, because the tunnel(s) are closed (and the tunnel(s) retain the archwire(s), there may be no need for the wings or other component for securing a ligature tie or the like thereon. Therefore, in an embodiment of the invention, the bracket does not include any components for securing a ligature tie or the like thereon.

As is shown in FIG. 3, the system 10 includes a plurality of brackets 12 secured on a patient's teeth. In many prior art bracket systems, different types of brackets (different shape, different slot prescription and different anatomy) were secured on different teeth. However, in a preferred embodiment of system 10, all of the teeth to be corrected include a bracket 12 secured thereon (e.g., molars, premolars, canines, lateral incisors and central incisors, etc.). It will be understood that the brackets 12 may be different sizes, but that each of the brackets 12 have the same design, as is shown in FIG. 3. Since the tunnels 14 and 18 are round (and not rectangular), super-elastic archwires 16a and 16b can be threaded through all of the brackets 12 starting at the midline and continuing posteriorly. In other words, the archwires 16a and 16b can be positioned by inserting both ends at the midline into the mesial openings of the tunnels 14 and 18, respectively, of the central incisor brackets 12 and then threaded posteriorly through the other brackets 12. Therefore, after all of the brackets 12 have been threaded, the archwires 16a and 16b extend continuously through all of the brackets 12 of the system and extend from the molar(s) on one side of the arch through the tunnel 14 or 18 associated with each intervening tooth and to the molar(s) on the other or opposing side. However, in an alternative embodiment, the archwires can be segmented.

In use, because the secondary tunnels 18 are closer to the facial surfaces of the teeth, secondary or supplemental archwire 16b is typically threaded first, followed by main archwire 16a, It will be understood that the terms "main" and "secondary" are not used herein to infer that one tunnel or archwire is more important or provides more effect or influence than the other. These terms are only used to aid in the understanding of the invention.

It will be understood that the use of the second archwire 16b provides for more rotational control and efficiency as it aids the first or main archwire 16a in straightening the teeth as both archwires 16a and 16b regain their initial shape via the shape memory properties inherent in super-elastic materials. In a preferred embodiment, the archwires 16a and 16b are made of nickel titanium. However, this is not a limitation on the present invention and other shape memory alloys or materials can be used. The second tunnel 18 is essentially a "partner" that allows the operator to add a second archwire 16b to the system for faster and more efficient tooth movement, e.g., rotations of teeth. It will be understood that the system 10 can be used with only one archwire 16a.

Threading the main archwire 16 through the tunnels 14 increases operator efficiency, decreases the chance for patient/operator injury with instruments and increases patient comfort because the forces related to ligating traditional brackets are unneeded. At adjustment visits, the wires can be removed the same way that they are inserted (threaded) which also provides for more efficiency, less chance of injury and less discomfort for the patient.

It will be understood by those skilled in the art, that in many cases or treatments of a patient (e.g., in a case where the teeth are crooked and no spaces need to be closed) nothing other than the friction of the superelastic archwires 16a and/or 16b within the tunnels 14 and/or 18 is necessary to hold the archwires 16a and/or 16b in place. However, some cases may require further aid in moving the teeth. This may be accomplished through the use of wings 22 and 24 and the spaces 23 and 25 defined between the wings 22 and 24 and the base 20. The wings 22 and 24 can be used in a number of different situations. For example, when a patient needs space between teeth closed, the treating doctor may need to use some type of elastic, such as what is called a power chain 26. All components that are used to retain the wire 16 on or in the bracket 12, including ligatures ties, power chains, clips, elastomeric rings and the like are numbered herein as 26 even though it is actually a power chain that is shown and numbered 26 in FIG. 9. A power chain 26 is an elastic chain that is placed on each of the brackets 12 in the area of the teeth where the space is to be closed. In other words, the treating doctor only places the power chain or elastics on some of the brackets 12. In another case, the power chain can be used on all of the brackets 12 on the upper or lower teeth. It will be understood by those skilled in the art that the wings 22 and 24 are used to retain the power chain or elastic on the bracket 12 and over the archwire 16a or 16b, This allows the power chain to exert forces that consolidate and pull the teeth towards one other.

Figure 4:
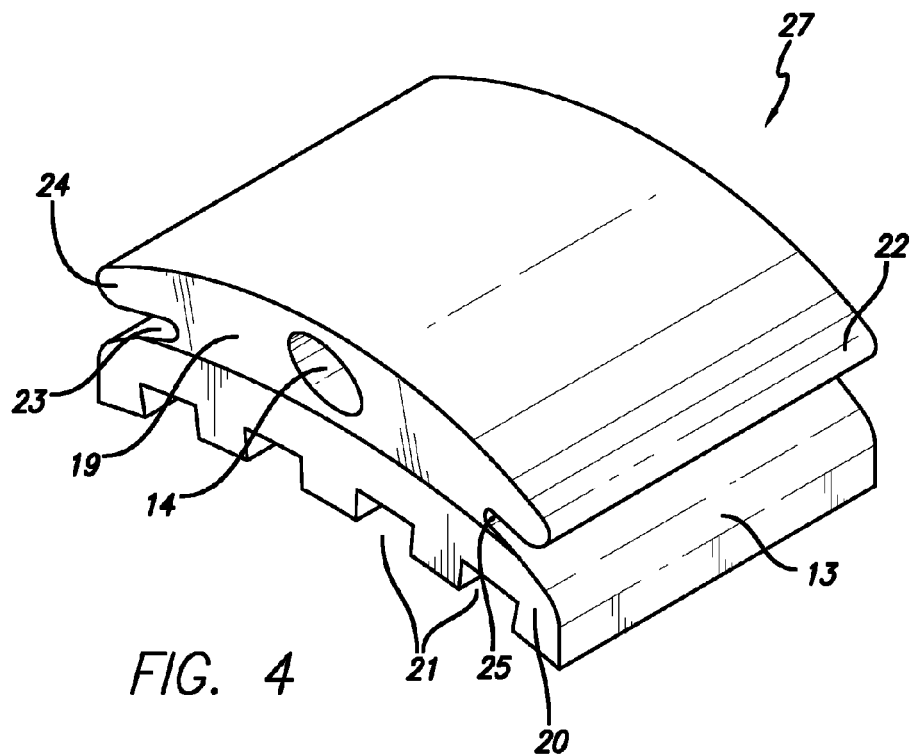
FIGS. 4 is a perspective view of an orthodontic bracket having one archwire tunnel, in accordance with a preferred embodiment of the present invention.
Figure 5:
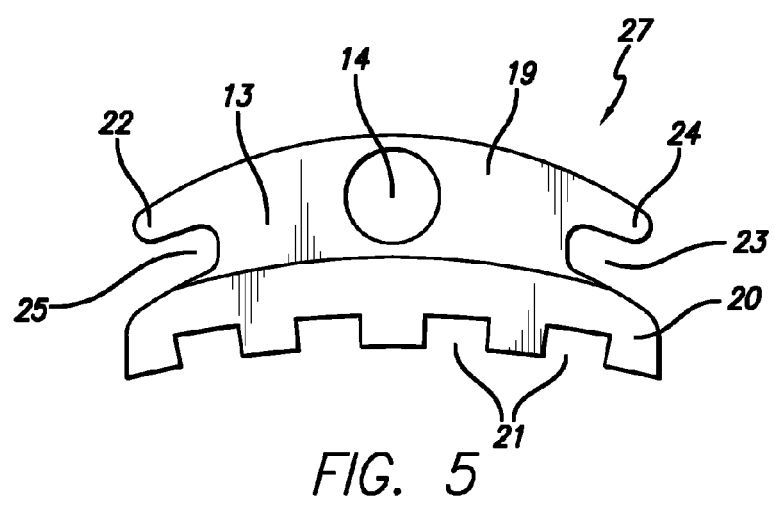
FIG. 5 is a side elevational view of the bracket of FIG. 4.
Figure 6:
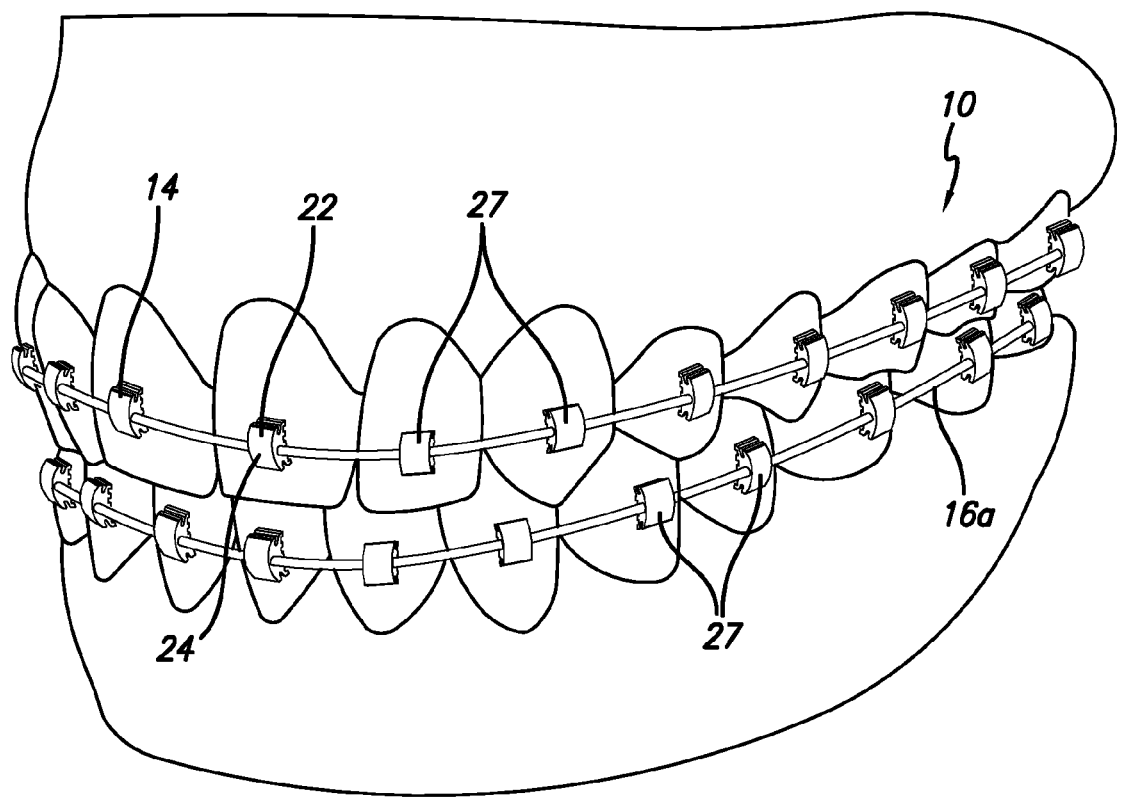
FIG. 6 is a perspective view of a plurality of the brackets shown in FIG. 4 on a set of teeth.

FIGS. 4-6 show another bracket 27 for use in an orthodontic bracket system 10. This bracket 27 is similar to bracket 12, but only includes a main tunnel 14 and omits tunnel 18. Accordingly, like components for bracket 27 are numbered the same as the like components on bracket 12. As shown in FIGS. 4 and 5, in an embodiment of the invention, the outer faces 19 of the upper portion of bracket 27 extend upwardly at an angle from the base 20. This provides another face (besides the wings 22 and 24) for retaining the power chain, ligature ties or the like. However, this is not a limitation on the present invention. This feature can also be included on bracket 12.

In an exemplary embodiment, only archwires with a circular cross-section are used. Accordingly, in an exemplary procedure or treatment, brackets 12 or 27 are placed on a plurality of teeth in an arch and an archwire 16a is threaded through the main tunnel 14. Over the course of time, the teeth will move in accordance with the shape memory characteristics of the archwire 16a, After the teeth have reached the desired position, the brackets and archwire are removed. In this embodiment, during the course of treatment, square or rectangular archwires (or any archwire that affects the roots or provides torque) are never used.

Figure 7:
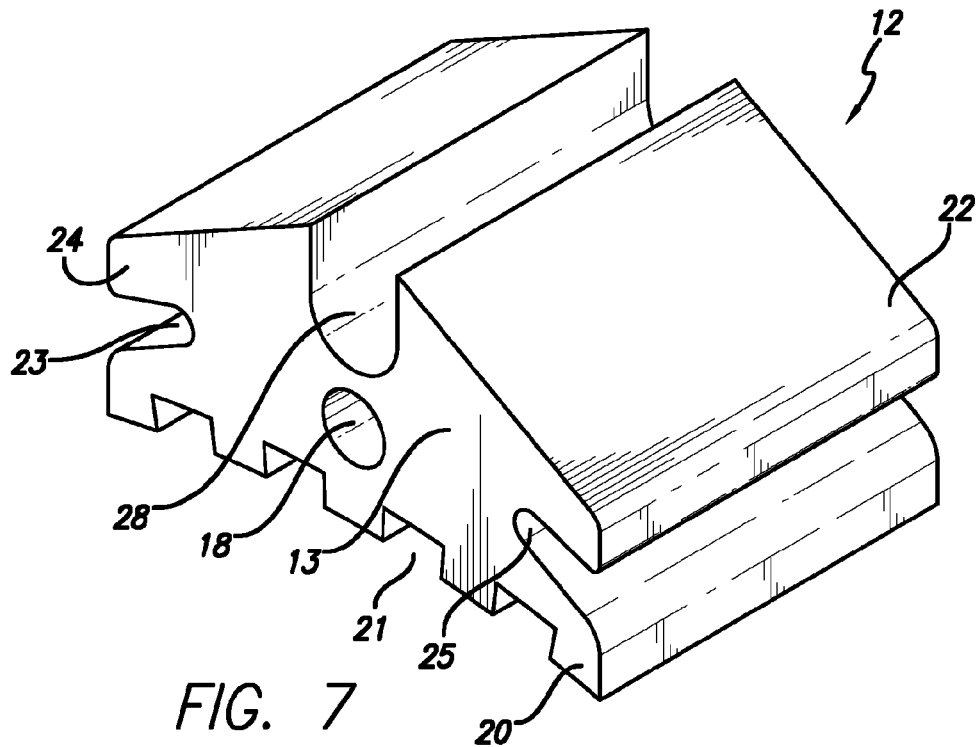
FIG. 7 is a perspective view of the bracket of FIG. 1 with the main tunnel converted to an open faced slot.

As shown in FIG. 7, in an embodiment of the invention, the treating doctor can use a bur or the like and open the most facial aspect of the main tunnel 14 (or both tunnels 14 and 18) to convert the bracket 12 or 27 into a bracket with an open faced slot 28, as shown in FIG. 7. This may be used in a situation where the treating doctor is using a relatively thick archwire 16a, which may prevent him/her from bending the archwire 16a over on itself to thread it through the two brackets 12 or 27 on the front teeth both upper and lower at the midline. In this situation, the doctor may convert the two front brackets 12 or 27 (or more brackets) into open slot 28 brackets. The archwire 16a can then be placed in the open slots 28 and threaded into the closed tunnels 14 in the next bracket 12 or 27 posterior to the two front brackets 12 or 27. In this situation, the doctor would need to use an elastic, which could be a power chain 26 (see FIG. 9), a regular ligature tie or the like, retained on the wings 22 and 24 to hold the wire in the slots 28.

Figure 8:
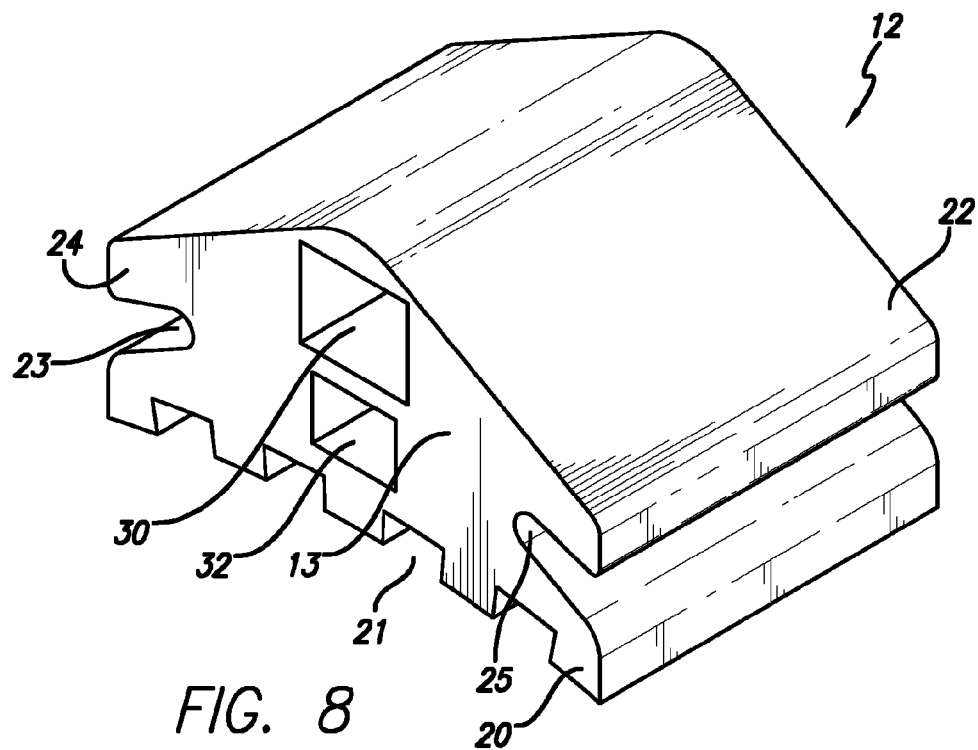
FIG. 8 is a perspective view of an orthodontic bracket having two rectanguarl shaped archwire tunnels, in accordance with another preferred embodiment of the present invention.
Figure 9:
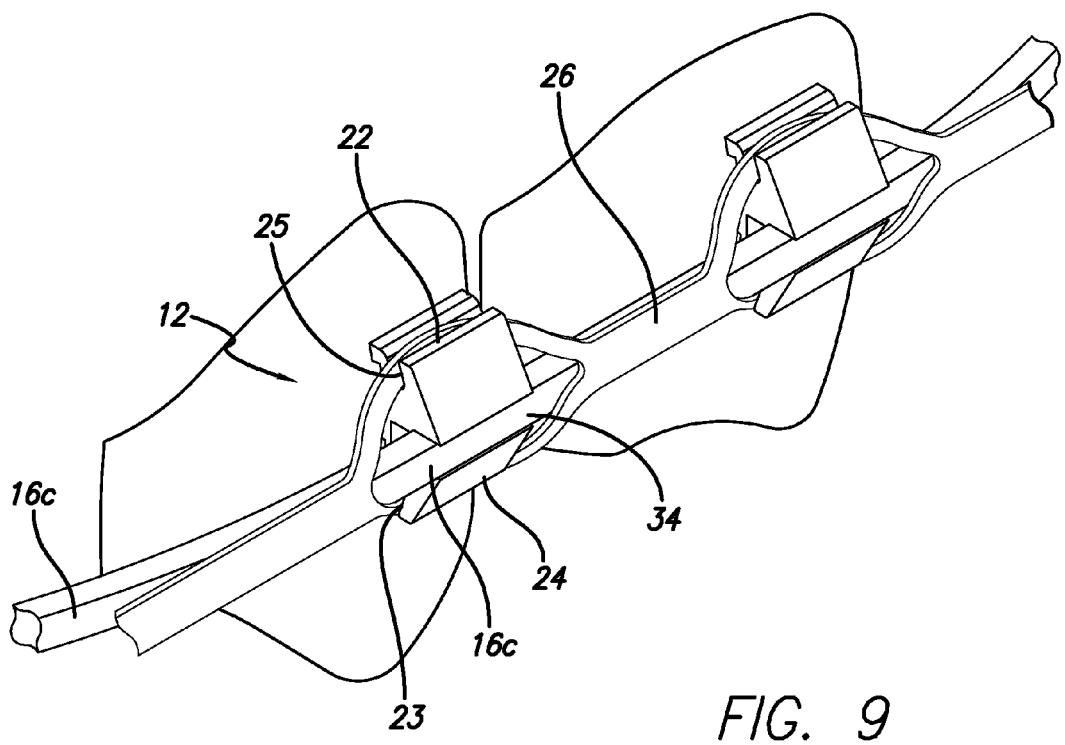
FIG. 9 is a perspective view of two of the brackets of FIG. 8 with the main tunnels converted to open faced slots and mounted on teeth.

As shown in FIGS. 8 and 9, in another embodiment, the brackets 12 can include rectangular or square shaped tunnels 30 and 32 (bracket 27 can be designed this way as well). Any non-circular shape is within the scope of the present invention. This allows the treating dentist to change treatment during the length of time that the brackets 12 or 27 are on the patient's teeth. For example, the dentist may start by placing round archwires 16a and/or 16b through the closed tunnels 30 and/or 32. In this case, the archwires 16a and/or 16b are threaded as described above by bending the wire so that the two halves are approximately parallel and threading the wire(s) through at the midline. Because the wires are round they can spin within the tunnels 14 and or 18 as they are threaded until they find their natural resting position as a result of their superelastic properties. However, at some point during treatment, the dentist may desire to place more torque on the roots of the teeth and may want to use rectangular archwires 16c, Rectangular wires can not be threaded through the closed rectangular tunnels 30 and 32 from the midline because they cannot spin and find their natural resting position. So, the dentist can convert one or both of the tunnels 30 and 32 as described above (on all of the brackets 12 or 27) into an open faced slot 34, as shown in FIG. 9. Once this is done, the rectangular wire 16c can be retained in the slots 34 using a power chain 26, ligatures or the like that are retained on the wings 22 and 24. In another embodiment one tunnel may be circular and the other be rectangular or square in cross-section.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An orthodontic bracket comprising:
   a main body portion having first and second tunnels extending transversely therethrough, wherein the first and second tunnels each have a circular cross-section, wherein the main body portion includes a base that has a bottom surface that is adapted to be bonded to a facial surface of a tooth such that the first and second tunnels extend approximately parallel to the facial surface, wherein the main body portion does not include any tunnels extending transversely therethrough that include a non-round and enclosed cross-section, and
   a pair of opposing retention members extending from the main body portion in a direction that is approximately perpendicular to an axis defined by the first tunnel, wherein the retention members each include at least one arm that extends outwardly from the main body portion and defines a gap with the base.

2. The bracket of claim 1 wherein the bracket does not include an open faced slot.

3. The orthodontic bracket of claim 2 in combination with a round archwire extending through the first tunnel.

4. The orthodontic bracket of claim 3 wherein the first and second tunnels extend approximately parallel to one another.

5. The orthodontic bracket of claim 1 wherein the second tunnel is positioned between the first tunnel and the bottom surface.

6. The orthodontic bracket of claim 5 wherein the first tunnel has a larger diameter than the second tunnel.

7. The orthodontic bracket of claim 1 wherein the base has a single undercut defined therein.

8. An orthodontic bracket system for correcting the teeth in an arch that includes molars, premolars, canines, lateral incisors and central incisors, the system comprising: a plurality of brackets that each include a main body portion having a base with a bottom surface and first and second tunnels extending transversely therethrough, wherein the first and second tunnels of each bracket each have a circular cross-section, wherein when each bracket is bonded to a facial surface of a tooth in the arch the first and second tunnels of each bracket extends approximately parallel to the facial surface of the tooth to which the bracket is bonded, wherein the main body portion does not include any tunnels extending transversely therethrough that include a non-round and enclosed cross-section,
   a first archwire extending through the first tunnels in each of the brackets, wherein the first archwire has a circular cross-section.

9. The system of claim 8 wherein none of the brackets through which the first archwire extends include an open faced slot.

10. The system of claim 8 wherein brackets are adapted to be bonded to at least one molar, at least one premolar, at least one canine, at least one lateral incisor and at least one central incisor.

11. The system of claim 8 wherein the first and second tunnels extend approximately parallel to one another.

12. The system of claim 8 further comprising a second archwire extending through the second tunnels in each of the brackets, wherein the second archwire has a circular cross-section.

13. The system of claim 12 wherein the second tunnel is positioned between the first tunnel and the bottom surface.

14. The system of claim 8 wherein each of the brackets further comprise a pair of opposing retention members extending from the main body portion in a direction that is approximately perpendicular to an axis defined by the first tunnel, wherein the retention members each include at least one arm that extends outwardly from the main body portion and defines a gap with the base.

15. An orthodontic bracket comprising:
   a main body portion having first and second tunnels extending transversely therethrough, wherein the first and second tunnels each have a round cross-section, wherein the main body portion includes an upper portion and a base that has a bottom surface that is adapted to be bonded to a facial surface of an anterior tooth such that the first and second tunnels extend approximately parallel to the facial surface, wherein the second tunnel is positioned between the first tunnel and the bottom surface, and
   first and second opposing retention members extending from the upper portion, wherein a plane bisects the first and second tunnels longitudinally and wherein the first retention member is positioned on a first side of the plane and the second retention member is positioned on a second side of the plane, wherein the first and second retention members each include at least one arm that extends outwardly from the main body portion and defines a gap with the base.

16. The orthodontic bracket of claim 15 in combination with a first round archwire extending through one of the first and second tunnels.

17. The orthodontic bracket of claim 16 in combination with a second round archwire extending through the other of the first and second tunnels.

18. An orthodontic bracket system for correcting the teeth in an arch that includes molars, premolars, canines, lateral incisors and central incisors, the system comprising:
   a plurality of brackets that each include a main body portion having first and second enclosed tunnels extending transversely therethrough, an upper portion, and a base that has a bottom surface, wherein when each bracket is bonded to a facial surface of a tooth in the arch the first and second tunnels of each bracket extend approximately parallel to the facial surface of the tooth to which the bracket is bonded, wherein the second tunnel in each bracket is positioned between the first tunnel and the bottom surface, and wherein each bracket includes first and second opposing retention members extending from the upper portion, wherein a plane bisects the first and second tunnels longitudinally and wherein the first retention member is positioned on a first side of the plane and the second retention member is positioned on a second side of the plane, wherein the first and second retention members each include at least one arm that extends outwardly from the main body portion and defines a gap with the base,
   a first archwire extending through one of the first or second tunnels in each of the brackets.

19. The system of claim 18 wherein none of the brackets through which the first archwire extends include an open faced slot.

20. The system of claim 18 wherein brackets are adapted to be bonded to at least one molar, at least one premolar, at least one canine, at least one lateral incisor and at least one central incisor.

21. The system of claim 18 further comprising a second archwire extending through the other of the first or second tunnels in each of the brackets.

22. The system of claim 18 wherein the first and second tunnels in each of the brackets have a circular cross-section.

* * * * *